(12) United States Patent
Smith

(10) Patent No.: US 6,368,564 B1
(45) Date of Patent: Apr. 9, 2002

(54) APPARATUS FOR INCORPORATING AIR MODIFYING AGENTS

(75) Inventor: Nigel Peter Smith, Wellington (GB)

(73) Assignee: Globol Chemical (uk) Limited, Devon (GB)

( * ) Notice: Subject to any disclaimer, the term of this patent is extended or adjusted under 35 U.S.C. 154(b) by 0 days.

(21) Appl. No.: 09/297,252

(22) PCT Filed: Oct. 22, 1997

(86) PCT No.: PCT/GB97/02915

§ 371 Date: Jun. 25, 1999

§ 102(e) Date: Jun. 25, 1999

(87) PCT Pub. No.: WO98/18503

PCT Pub. Date: May 7, 1998

(30) Foreign Application Priority Data

Oct. 28, 1996 (GB) .............................................. 9622354

(51) Int. Cl.$^7$ .............................. A61L 9/12; A61L 9/16; A61L 9/04
(52) U.S. Cl. .............................. 422/123; 422/4; 422/5; 239/34; 239/51.5; 429/7
(58) Field of Search ................................ 422/4, 5, 122, 422/123; 239/34, 35, 44, 51.5; 429/7, 188, 163, 167, 176, 307, 324

(56) References Cited

U.S. PATENT DOCUMENTS

| | | | | | |
|---|---|---|---|---|---|
| 3,657,020 | A | * | 4/1972 | Harrah | 429/90 |
| 3,739,464 | A | * | 6/1973 | Ellenberger | 429/7 |
| 4,383,951 | A | * | 5/1983 | Palson | 239/35 |
| 4,460,663 | A | * | 7/1984 | Stutzbach et al. | 429/151 |
| 4,707,338 | A | * | 11/1987 | Spector | 422/124 |
| 5,155,144 | A | | 10/1992 | Manganaro et al. | |
| 5,429,271 | A | * | 7/1995 | Porter | 239/34 |
| 5,431,885 | A | * | 7/1995 | Zlotnik et al. | 422/122 |
| 5,498,397 | A | * | 3/1996 | Horng | 422/124 |

FOREIGN PATENT DOCUMENTS

| | | | |
|---|---|---|---|
| EP | 0 327 932 | 2/1989 | |
| EP | 0 331 518 | 9/1989 | |
| EP | 0 645 148 A1 | 3/1995 | |
| EP | 0 669 137 A1 | 8/1995 | ............. A61L/9/12 |
| FR | 2 724 578 | 3/1996 | |
| GB | 2 236 482 A | 4/1991 | |
| GB | 2 292 250 A | 2/1996 | |
| GB | 2 297 909 A | 8/1996 | |
| HU | 194 054 | 11/1988 | |
| HU | 216 282 B | 10/1995 | |

OTHER PUBLICATIONS

Novelty Search Report—Hungarian Patent Office—Appl. No. P 00 00345—Dated: Mar. 31, 2000.

* cited by examiner

Primary Examiner—Robert J. Warden, Sr.
Assistant Examiner—Kaj K. Olsen
(74) Attorney, Agent, or Firm—Marshall, Gerstein, & Borun

(57) ABSTRACT

A method and apparatus are described for dispersing an air modifying agent (e.g. a fragrance) in air. The air modifying agent and an electrolyte are entrained in a gel-based aqueous reservoir (7), which contacts a pair of electrodes (8, 9) which are +ve and −ve with respect to each other to provide an electrical potential between the electrodes. The electrical potential powers a small motor and fan (13, 14) which disperse the air modifying agent from the surface of the reservoir (7) to the surrounding atmosphere via apertures (16) in a housing (10) of the apparatus. The electrical potential can power additional or alternative electrical devices such as lighting and heating devices, and the arrangement may be such that the extent of exhaustion of the air modifying agent from the reservoir (7) corresponds generally to the extent of exhaustion of electrode (8, 9) activity, whereby the operability of the electrical device indicates the presence of air modifying agent in the reservoir (7).

35 Claims, 2 Drawing Sheets

APPARATUS FOR INCORPORATING AIR MODIFYING AGENTS

FIELD OF THE INVENTION

This invention relates to a method and apparatus which incorporates air modifying agents, particularly, though not solely, air freshening, fragrancing and/or deodorizing substances, or insecticides.

PRIOR ART

It is well known to provide sources of air freshening, fragrancing and/or deodorizing substances and insecticides in a vaporisable form such that, upon vaporisation of appropriate substance, an active vapor is dispersed into the surrounding air.

Often it is desirable to use an electrically powered fan or heater to aid vaporisation and/or dispersion and to this end a small battery driven power source is typically provided. However batteries-often lead to inconvenience in that they constitute a further component and, in use, run down or decay and have to be replaced

DESCRIPTION OF THE INVENTION

The present invention seeks to address at least some of the shortcomings occasioned by the use of batteries whilst, at the same time, providing a novel, active means of determining the presence of, and preferably dispersing, an air modifying agent.

Accordingly, in one aspect, the invention provides a method for dispersing an air modifying agent in air, the method comprising the steps of entraining, the air modifying agent in air modifying agent reservoir means to provide a source of the air modifying agent; entraining an electrolyte in electrolyte reservoir means to provide a source of an electrolyte; providing a plurality of electrode means arranged to be in electrical contact with each other via the electrolyte such that in use the arrangement generates an electrical potential; providing an electrical dispersion device operable by the electrical potential to effect or assist dispersion of the air modifying agent from an outlet of the air modifying agent reservoir means into an air space; and disposing the said reservoir means such that the outlet of the air modifying agent reservoir means is in relative proximity to the electrical dispersion device for said dispersion of the air modifying agent into the air space; wherein the electrolyte reservoir means and the electrode means are not present solely as a discrete sealed battery unit removably electrically connected to the electrical dispersion device. The above steps are performable in a variety of orders, as will be understood by one of skill in this art; they are not limited to the order recited above.

According to a second aspect, the invention provides apparatus for dispersing an air modifying agent in air, the apparatus comprising: a housing partially enclosing an air space; electrolyte reservoir means disposed within the housing and providing a source of an electrolyte; a plurality of electrode means disposed within the housing and arranged to be in electrical contact with each other via the electrolyte such that in use the arrangement generate an electrical potential; air modifying agent reservoir means disposed within the housing and providing a source of the air modifying agent; and an electrical dispersion device operable by the electrical potential to effect or assist dispersion of the air modifying agent from an outlet of the air modifying agent reservoir means into the air space and thence into surrounding ambient air; wherein the outlet of the air modifying agent reservoir means is disposed in relative proximity to the electrical dispersion device for said dispersion of the air modifying agent into the air space and the electrolyte reservoir means and the electrode means are not present solely as a discrete sealed battery unit removably electrically connected to the electrical dispersion device.

The air space partially enclosed by the housing is in air flow comnmunication with the surrounding ambient air, e.g. via one or more apertures in the housing. In this way, dispersal of the air modifying agent into the air space leads to dispersal of the agent into the surrounding air.

The electrolyte reservoir means is suitably a dimensionally stable solid or semisolid substance or structure capable of retaining within its volume a solvent such as water, containing an electrolyte (e.g. a salt) dissolved therein. The arrangement permits the dissolved electrolyte to contact the electrode means for establishing the electrical contact. Alternatively, but less preferably, the electrolyte reservoir means may be a volume of a liquid carrier, e.g. water. The air modifying agent reservoir means may also be a volume of a liquid carrier, e.g. water, but is more suitably a dimensionally stable solid or semisolid substance or structure capable of retaining within its volume an air modifying agent, while permitting the air modifying agent to exit from an outlet, to disperse the air modifying agent into the air space and thence into the surrounding air. The outlet typically comprises a surface of the reservoir which is in contact with the air space (suitably over a large surface area), from which the air modifying agent disperses in vapor or mist form into the air space and to which further air modifying agent is drawn from the interior of the reservoir means.

Examples of such reservoir means include gels (for example natural or synthetic polysaccharide gels), absorbent mats, felts or pads, wicks, bulk liquid water or any combination thereof. The reservoir means(other than bulk liquid water) may be permanently solvated (e.g. hydrated) or may be stored in a relatively unsolvated (e.g. dehydrated) form and solvated when required for use.

The reservoir means typically occupy a major portion of the base of the housing, and are suitably disposed in the housing in such a way as to leave substantially no intervening space between each other. More particularly, the electrolyte reservoir means may underlie and/or be in contact with the air modifying agent reservoir means to support the same. Where the reservoir means are identical, or are composed of substances (e.g. gels) which are miscible to form a unitary form or structure, the two reservoir means may preferably be combined into a generally unitary form or structure, provided always that the form or structure permits dispersion of the air modifying agent from it in relative proximity to the electrical dispersion device. The phrase "in relative proximity" herein refers generally to proximity of the outlet of the air modifying agent reservoir means to the electrical dispersion device, relative to the major part of the volume of the electrolyte reservoir means (or, when the two reservoir means are combined into a generally unitary form or structure, the major part of the volume of the unitary reservoir means).

The air modifying agent can be selected, for example, from air freshening substances, air fragrancing substances, air deodorising substances, anti-bacterial agents and insecticides. For air freshening applications, the air modifying agent will typically comprise a gelled, fragrant substance formed by combining water, gelling agent and a fragrance. The gelling agent and water comprise the air modifying agent reservoir means. Surprisingly, we have found that when using carrageenan as a gelling agent, even in concentrations of 2.5% by weight, sufficient electrolytic activity is generated, using a variety of electrodes, to power a small electric motor with fan. Such a gelling agent and water can therefore also comprise the electrolyte reservoir means, and this leads to the option, mentioned above, that the two reservoir means can be combined into a generally unitary gelled form. It is known that carrageenan is derived from seaweed and it is believed that the salts which occur naturally in seaweed (which include potassium chloride) impart the electrolytic properties to the gelling agent.

Suitable forms of carrageenan include DANAGEL DKL sourced from FMC Litex Limited. This comprises a carrageenan base with calcium acetate and locust bean gum as additives. Other carrageenan based gelling agents could be substituted including FMC Litex products coded VG11S, AF2 and AF10.

Other gelling agents, not so rich in natural salts, may also be used but will require the addition or electrolytes such as, for example, KCl, NaCl and $CuSO_4$. These electrolytes would be mixed with the gelling agent, a bulking agent (water) and the fragrance, the various constituents being selected to ensure a block of vaporisable, fragrant substance is achieved which has sufficient electrolytic activity to, in combination with the chosen electrodes, power the electrical dispersion device chosen to effect or at least stimulate vaporisation.

The air modifying agent need not initially be in the form of a gel. Commonly such agents are also derived from liquids—either in bulk form or impregnated in mats. If a liquid source of air modifying agent is to be incorporated in apparatus according to the invention then such liquid will be selected for its electrolytic properties or may have electrolytic properties imparted thereto by the addition of suitable electrolytes. In the case of pads, the electrolyte, and even the air modifying agent, may be provided in dry form and activated by the addition of water or other solvent.

The electrode means are in contact with at least the electrolyte reservoir means, and optionally also with the air modifying agent reservoir means. This latter option can enable a particularly compact arrangement of parts within a housing.

The electrode means may take any conventional form and be constructed from any conventional electrode material suitable for an electrolyte cell. The electrode means may, for example, comprise a pair of rod members, having the desired electrical characteristics. The rod members are preferably immersed into the electrolyte. Alternatively, one of the electrodes may for example be formed by the inner surface of the housing, to enable as large an electrode surface area as possible. One or more of the electrodes may, as a further alternative, be provided in granule or particulate form, to maximise the surface area in contact with the electrolyte.

When in granulated form, a conducting carrier is advantageously provided to ensure charges from the individual granules are relayed to a common terminal. By way of example, carbon granules could be held in contact with aluminium foil using a mesh, the mesh allowing the electrolyte to flow about the granules without physically displacing the same.

As will be readily understood, it is necessary for the electrode means to have distinct and different electronegativities in order to generate the electrical potential in the manner of an electrochemical cell. The materials from which the electrodes are constructed may, for example, be selected from zinc, carbon, copper or aluminium. The electrodes may comprise an inert substrate on which an active electrode surface material is provided. The electrolyte reservoir means typically includes conventional antidepolarisation and/or antiplating agents which inhibit depolarisation of the electrochemical cell and/or plating of the electrode means, at least for a time sufficient to enable the bulk of the air modifying agent to be dispersed.

The electrolyte is suitably a water-soluble sale such as a salt of a hydrophobic cation (e.g. a potassium, sodium, ammonium or copper salt). Typical salts include potassium chloride, sodium chloride and copper sulphate. In certain naturally occurring gels, such as carrageenan, salts such as potassium chloride occur naturally; such gels are therefore preferred for use as electrolyte reservoir materials in the present invention. If electrolyte reservoir materials are used which do not inherently contain suitable electrolytes in sufficient amounts, the electrolyte must be added.

The electrical dispersion device is advantageously a fan or other device for causing a flow of air across the outlet (e.g. surface) of the air modifying agent reservoir means. The fan is driven by a small electrical motor powered by the electrical potential generated by the electrochemical cell. Alternatively or additionally, the electrical dispersion device may be a heating device, which assists in vaporisation of the air modifying agent.

The invention enables an electrochemical cell to power the dispersion of an air modifying agent from a reservoir of The said agent, in a more compact, convenient and efficient manner than known hitherto. As mentioned above, it is particularly desirable that the electrode means are in contact not only with the electrolyte but with the source of air modifying agent, as this enables a particularly compact and efficient structure, especially when the air modifying agent reservoir means can itself contain an electrolyte in addition to the electrolyte present in the electrolyte reservoir means.

The arrangement may suitably be such that the electrical dispersion device; the electrolyte reservoir means and the air modifying agent reservoir means are selected so that on operation of the electrical dispersion device the extent of exhaustion of the air modifying agent from the air modifying agent reservoir means corresponds generally to the extent of exhaustion of electrode activity, whereby the operability of the electrical dispersion device indicates the presence of air modifying agent in the air modifying agent reservoir means. An electrical lighting device may, additionally or alternatively, be connected to be powered by the electrical potential generated by the electrode means, to provide a visual indication of the present of air modifying agent.

Moreover, the lighting device may provide an attractive and useful function, in illuminating the apparatus. This illumination may conveniently take place from the interior of the apparatus, which in this case will have at least part of its housing made from a translucent material. Most conveniently, the air modifying agent reservoir means and/or the electrolyte reservoir means may be translucent and the electrical lighting device, which may of course also provide a dispersing effect through any heat it may produce, is immersed therein to illuminate the reservoir means from within.

In general, a variety of electrical devices can be readily envisaged, which can indicate the presence of air modifying agents in a source thereof.

Thus, in a third aspect, therefore, the invention provides a method of indicating the presence of an air modifying agent, said method comprising:

placing electrode means in contact with a source of air modifying agent and in contact with an electrolyte in a manner such that the combination of said electrode means and said electrolyte generates an electrical potential; and providing an electrical consumer operable by said electrical potential to indicate the presence of said air modifying agent.

The consumer is preferably selected to not only indicate the presence of the air modifying agent but also to effect or assist dispersion thereof.

Preferably said method further comprises mixing said air modifying agent with said electrolyte.

Alternatively said method comprises retaining said electrolyte and said air modifying agent separately, but in juxtaposition.

In a still further aspect the invention provides apparatus for indicating the presence of an air modifying agent, said apparatus comprising:

an air modifying agent;

an electrolyte;

electrode means contactable or in contact with said air modifying agent and said electrolyte to, in use, generate an electrical potential; and an electrical consumer operable by said electrical potential to, in use, indicate the presence of said air modifying agent;

The consumer may simply be a static device such as a light emitting diode (tabs connected to suitable electrodes and immersed into the electrolyte. However, the consumer preferably has a further function, namely to effect or assist dispersion of the air modifying agent and, to this end, preferably comprises an electrically powered fan-or the like.

The air modifying agent is preferably mixer with said electrolyte but, alternatively, may be retained separately but in juxtaposition. In the case of gel-based or modifying agents the gelling agent may be selected having-regard to its electrolytic properties. Gelling agents displaying electrolytic properties include carrageenan.

The electrode means may comprise a pair of rod members, having the desired electrical characteristics, which, in use, are immersed into the electrolyte. Electrodes found suitable for use with carrageenan include carbon and zinc electrodes. By way of one alternative, one of the electrodes may be formed by the inner surface of a housing containing the electrolyte and air modifying agent in undispersed form.

DESCRIPTION OF PARTICULAR EMBODIMENTS

Specific forms of apparatus embodying the invention will now be described, without limitation and purely by way of example, with reference to the accompanying drawings, in which.

Figure 1:
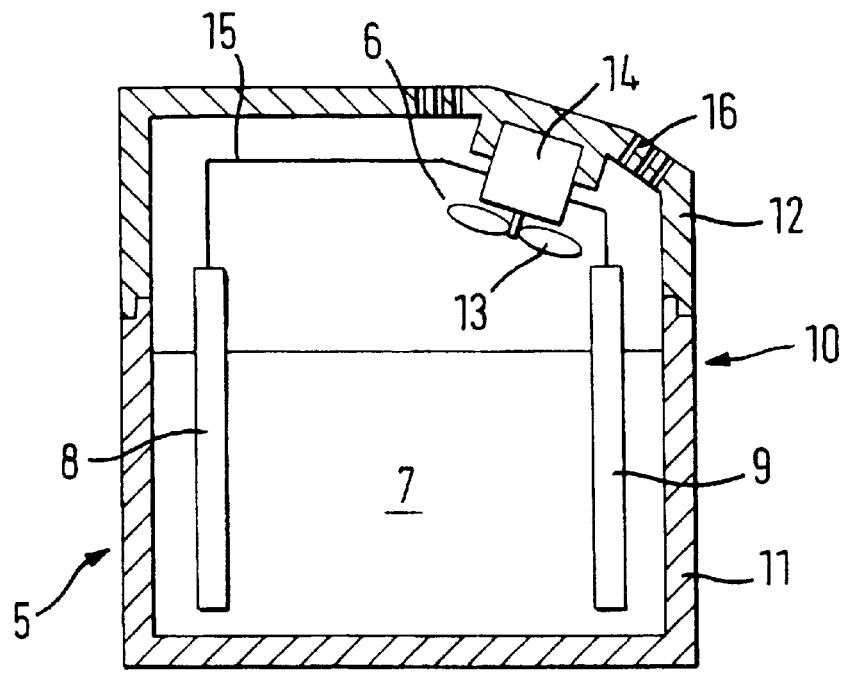
FIG. 1 shows a cross-sectional schematic view through is one form of apparatus embodying the invention for dispersing an air modifying agent.

Referring firstly to FIG. 1 of the drawings, according to the invention apparatus 5 is provided for dispersing an air modifying agent, the apparatus 5 including an electrical consumer 6 operable to, in use, effect or at least assist dispersal of an air modifying agent (shown undispersed in a unitary reservoir as 7). To this end, the apparatus further includes an electrolyte reservoir combined with the air modifying agent reservoir 7; and a pair of electrodes 8 and 9 contactable or in contact with both the air freshening agent and the electrolyte to generate an electrical potential to drive the consumer 6.

In the form shown, the apparatus 5 is included in a housing 10 which comprises a base part 11 and an interlocking lid 12. The consumer 6, which is shown as a fan 13 driven by an electric motor 14, is mounted within the lid 12.

It will be appreciated that the consumer 6 could be a number of alternative forms of electrically driven apparatus including, for example, a lamp or electrical resistance heater.

In the form shown in FIG. 1, the electrodes 8 and 9 comprise rods, one being formed from zinc and the other of carbon. These are placed in spaced positions within the electrolyte reservoir 7 and are placed in circuit with the motor 14 using electrically conducting leads 15.

Other forms of electrode may be used and may be more suitable, particularly if the composition of the electrolyte and/air modifying agent is changed. For example, combinations of Cu/Zn or Cu/C may prove effective and we have found that Al can be substituted for Zn as the negative electrode. Steps may need to be taken to inhibit plating or polarisation of one or both of the electrodes to ensure the electrodes are effective for a time sufficient to ensure the bulk of the air modifying agent is dispersed.

It is also envisaged that one or more of the electrodes may be in a form other than the rod form depicted and described. Generally, an increase in surface area give an increase in electrolytic activity, hence granular carbon works well as a positive electrode.

Turning now to FIG. 2, a further form of apparatus 20 is shown for dispersing an air modifying agent. In this embodiment the air modifying agent and the electrolyte are not intermixed but are held in juxtaposed reservoir of liquid water, 21 and 22 respectively, separated by membrane 24.

As with the embodiment previously described, the electrolyte in the reservoir 22, in combination with the selected electrodes, provides an electrical current to drive a consumer such as electric motor 25 driving fan 26.

In this particular embodiment, one electrode is formed by the housing 27 which is either formed from, or lined with, a material having the required degree of activity when combined with the other electrode 28 and the electrolyte in reservoir 22.

The electrode 28 is a central rod which passes through the air modifying agent 21, through membrane 24 and into the electrolyte 22. A seal 29 may be provided where the electrode 28 passes through the membrane 24 to prevent leakage of the air modifying agent into the electrolyte.

Electrically conducting leads 30 place the motor 25 in circuit with the electrodes.

Referring to FIG. 3, an arrangement generally similar to FIG. 1 is shown, except that a wick 32 and dispersion pad 33 are present to draw air modifying agent from the unitary reservoir 7. The outlet of the reservoir is thus the dispersion pad 33, which is in relatively close proximity to the fan 13, as opposed to the surfacer of the bulk of the reservoir, as in FIGS. 1 and 2.

To activate each form of apparatus the electrodes are lowered into the electrolyte and placed in circuit with the motor. As the motor powers the fan, the air modifying agent is vaporised and driven through outlet apertures 16, 31 in the housing 10, 27 respectively and into the ambient air surrounding the apparatus.

Figure 4:
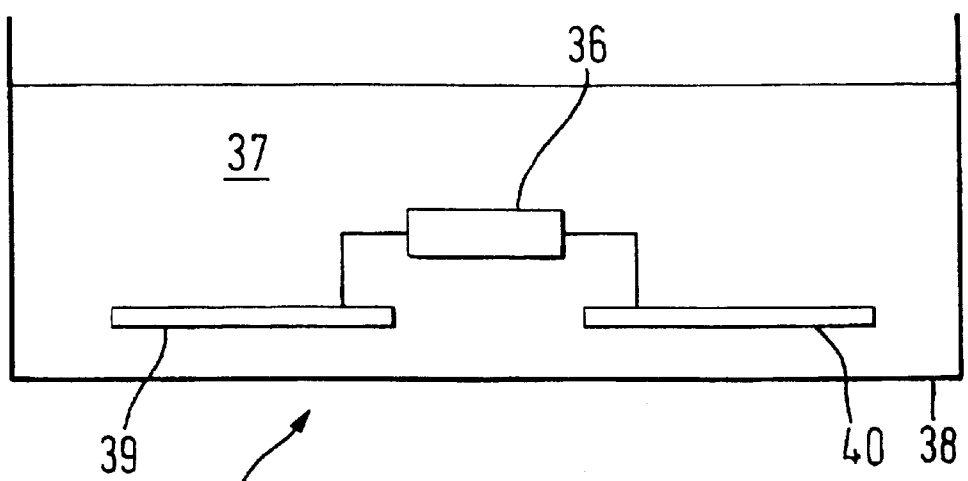
FIG. 4 shows a cross-sectional schematic view through a fourth, and very simple, form of apparatus embodying the invention.

Referring finally to FIG. 4, a very simple form of device 35 is shown which embodies the invention the device 35 does not include a fan or the like to assist dispersion of an air modifying agent but merely includes a light emitting diode (LED) 36 to indicate the presence of the air modifying agent.

In this embodiment the electrolyte is incorporated within a clear, air modifying gel 37, the gel being contained in turn, within a bowl or dish 38. The LED 36 is placed in circuit with electrodes 39 and 40 immersed within the gel/electrolyte 37 and is thus powered thereby.

Being, itself, immersed within the electrolyte the LED causes the gel to glow. As the gel vaporises the power available to the LED reduces until there is insufficient available to power the LED. This indicates the time to replace the device or to recharge the device with electrolyte/gel.

The embodiment shown in FIG. 4 not only provides a convenient device for dispersing air freshening, fragrancing and the-like agents, but would simultaneously provide a comforting night light.

Figure 2:
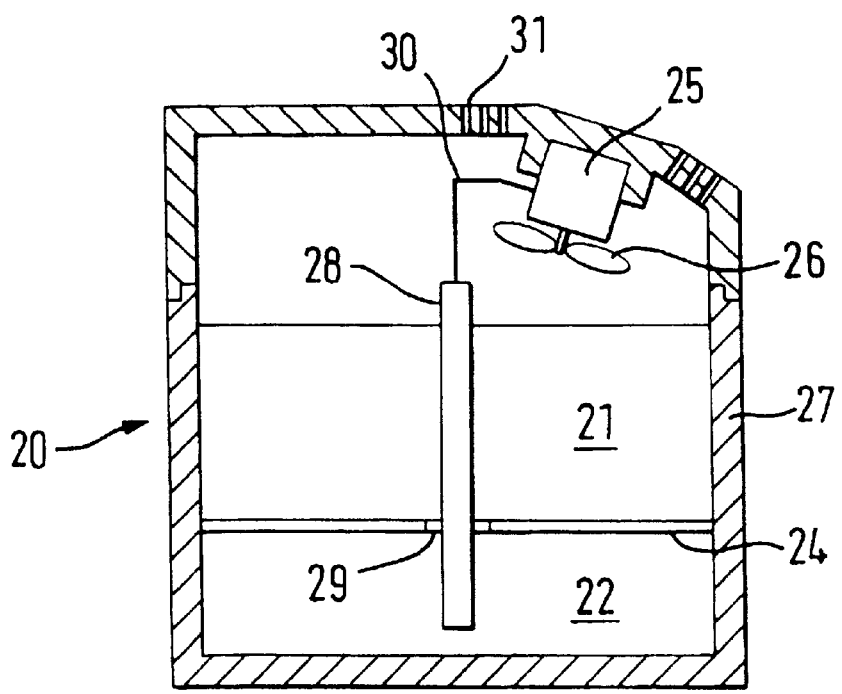
FIG. 2 shows a cross-sectional schematic view through a second form of apparatus embodying the invention for dispersing an air modifying agent.
Figure 3:
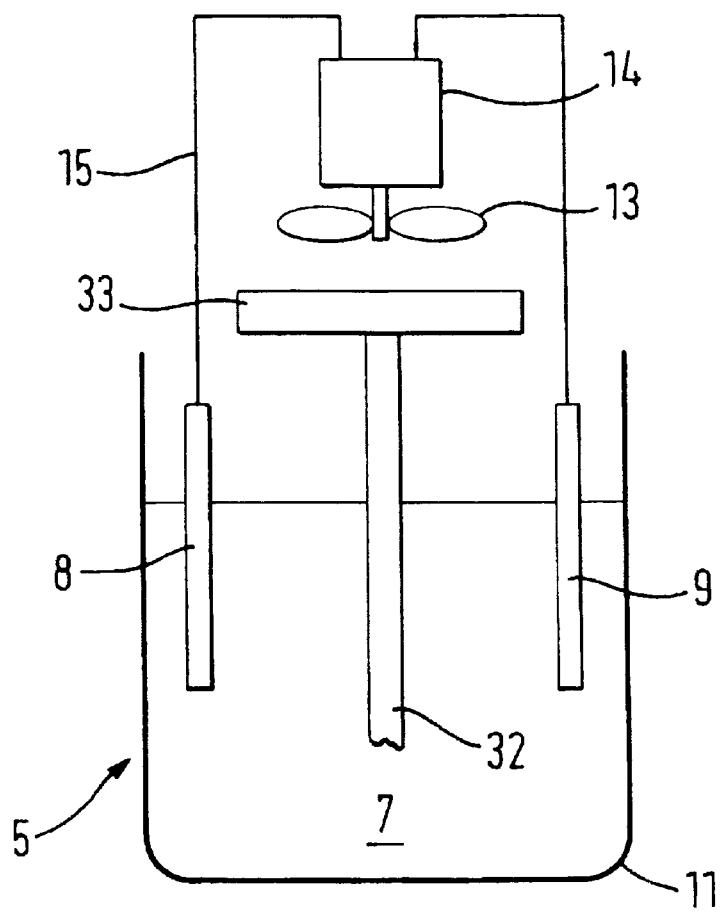
FIG. 3 shows a cross-sectional schematic view through a third form of apparatus embodying the invention for dispersing an air modifying agent.

The forms of apparatus shown in FIGS. 1, 2 and 4 preferably incorporate a gel which acts as a source of both air modifying agent and of electrolyte. In such cases it is desirable to select a gelling agent which has electrolytic properties. An example of such a gelling agent is carrageenan. We have found that carrageenan in amounts as low as 2.5 can generate sufficient electrolytic activity to power a small fan or an LED. suitable grades of carrageenan include DANAGEL DKL, VG11S, AF2 and AF10 sourced from FMC Litex Limited.

EXAMPLE

A form of air freshening apparatus substantially as shown in FIG. 1 was manufactured in order to prove the concept.

A air freshening gel was made up of the following composition:

| | |
|---|---|
| (i) | 2.5% gelling agent (DANAGEL DKL from FMC Litex Limited). |
| (ii) | 3% fragrance. |
| (iii) | 2% surfactant. |
| (iv) | 0.2% preservative. |
| (v) | Balance water. |

The above gel was placed in a plastics container and carbon (+ve) and zinc (-ve) rod electrodes immersed in spaced positions within the gel. This configuration produced an electric potential of 0.5 to 1 volts and a a current of 10 to 20 milliamps.

What is claimed is:

1. Apparatus for indicating the presence of an air modifying agent, said apparatus comprising:
   an air modifying agent;
   an electrolyte;
   electrodes contactable or in contact with said air modifying agent and said electrolyte to, in use, generate an electrical potential; and
   an electrical consumer operable by said electrical potential to, in use, indicate the presence of said air modifying agent.

2. Apparatus according to claim 1, in which the electrolyte comprises a carrageen-based gelling agent.

3. Apparatus according to claim 1, in which the electrolyte is a salt.

4. Apparatus according to claim 1 in which the air modifying agent is selected from the group consisting of air freshening substances, air fragrancing substances, air deodorizing substances, anti-bacterial agents, insecticides, and combinations thereof.

5. Apparatus according to claim 1 in which the electrodes comprise materials selected from the group consisting of zinc, carbon, copper, and aluminum.

6. Apparatus according to claim 1 in which the electrical potential generated is in the range of about 0.5 to about 1 V.

7. Apparatus according to claim 1 in which the electrical potential causes a current in the range of about 10 to about 20 mA.

8. Apparatus according to claim 1 in which the electrical consumer is selected from devices which cause a flow of air and devices which cause heat to be applied to the reservoir.

9. Apparatus according to claim 8, in which the heating device can also emit light.

10. Apparatus according to claim 1 in which the electrical consumer is an electrical lighting device.

11. Apparatus for dispersing an air modifying agent in air, the apparatus comprising:
    a housing partially enclosing an air space;
    an electrolyte-containing and air modifying agent-containing reservoir disposed within the housing and providing a source of an electrolyte and of an air modifying agent;
    a plurality of electrodes disposed within the housing and arranged to be in electrical contact with each other via the reservoir such that in use the arrangement generates an electrical potential;
    an electrical dispersion device operable by the electrical potential to effect or assist dispersion of the air modifying agent from an outlet of the reservoir into the air space and thence into surrounding ambient air;
    wherein the outlet of the reservoir is disposed in relative proximity to the electrical dispersion device for said dispersion of the air modifying agent into the air space, and the arrangement of electrodes, electrolyte, air modifying agent, and reservoir is disposed unsealed within the housing.

12. Apparatus according to claim 11 in which the outlet of the reservoir comprises a surface of the reservoir which is in contact with the air space.

13. Apparatus according to claim 11 in which the reservoir is selected from the group consisting of a volume of a liquid carrier, a dimensionally stable solid substance, a dimensionally stable semisolid substance, a dimensionally stable structure capable of retaining within its volume a solvent containing an electrolyte and air modifying agent dissolved therein, and combinations thereof.

14. Apparatus according to claim 11 in which the reservoir is selected from the group consisting of gels, absorbent mats, felts or pads, wicks, bulk liquid water, and combinations thereof.

15. Apparatus according to claim 14 in which the gel comprises water and a carrageen-based gelling agent.

16. Apparatus according to claim 11 in which the electrolyte is a salt.

17. Apparatus according to claim 11 in which the air modifying agent is selected from the group consisting of air freshening substances, air fragrancing substances, air deodorizing substances, anti-bacterial agents, insecticides, and combinations thereof.

18. Apparatus according to claim 11 in which the electrodes comprise materials selected from the group consisting of zinc, carbon, copper, and aluminum.

19. Apparatus according to claim 11 in which the electrical potential generated is in the range of about 0.5 to about 1 V.

20. Apparatus according to claim 11 in which the electrical potential causes a current in the range of about 10 to about 20 mA.

21. Apparatus according to claim 11 in which the electrical dispersion device is selected from devices which cause a flow of air and devices which cause heat to be applied to the reservoir.

22. Apparatus according to claim 21 in which the heating device can also emit light.

23. Apparatus according to claim 11 in which an electrical lighting device is electrically connected to be powered by the electrical potential.

24. Apparatus according to claim 23, in which the reservoir is translucent and the electrical lighting device is immersed in the reservoir.

25. Apparatus for dispersing an air modifying agent in air, the apparatus comprising:
   a housing partially enclosing an air space;
   an electrolyte-containing and air modifying agent-containing gel disposed within the housing and providing a source of an electrolyte and of the air modifying agent;
   a plurality of electrodes disposed within the housing and in contact with the gel, such that in use the arrangement generates an electrical potential;
   an electrical dispersion device operable by the electrical potential when the apparatus is in use, to effect or assist dispersion of the air modifying agent from the gel into the air space and thence into surrounding ambient air;
   wherein the gel is disposed in relative proximity to the electrical dispersion device for said dispersion of the air modifying agent into the air space.

26. Apparatus according to claim 25 in which the gel comprises water and a carrageen-based gelling agent.

27. Apparatus according to claim 25 in which the electrolyte is a salt.

28. Apparatus according to claim 25 in which the air modifying agent is selected from the group consisting of air freshening substances, air fragrancing substances, air deodorizing substances, anti-bacterial agents, insecticides, and combinations thereof.

29. Apparatus according to claim 25 in which the electrodes comprise materials selected from the group consisting of zinc, carbon, copper, and aluminum.

30. Apparatus according to claim 25 in which the electrical potential generated is in the range of about 0.5 to about 1 V.

31. Apparatus according to claim 25 in which the electrical potential causes a current in the range of about 10 to about 20 mA.

32. Apparatus according to claim 25 in which the electrical dispersion device is selected from devices which cause a flow of air and devices which cause heat to be applied to the gel.

33. Apparatus according to claim 32 in which the heating device can also emit light.

34. Apparatus according to claim 25 in which an electrical lighting device is electrically connected to be powered by the electrical potential.

35. Apparatus according to claim 34, in which the gel is translucent and the electrical lighting device is immersed in the gel.

* * * * *